United States Patent [19]

Vuncannon

[11] Patent Number: 4,717,870

[45] Date of Patent: Jan. 5, 1988

[54] SLASHER MOISTURE MONITORING SYSTEM

[75] Inventor: James W. Vuncannon, Randleman, N.C.

[73] Assignee: Burlington Industries, Inc., Greensboro, N.C.

[21] Appl. No.: 362,521

[22] Filed: Mar. 26, 1982

[51] Int. Cl.⁴ ............................................. G01R 27/22
[52] U.S. Cl. .................................. 324/65 R; 68/13 R; 118/712; 384/277
[58] Field of Search ................. 162/DIG. 6, 252, 262, 162/263, DIG. 10; 324/61 R, 65 R; 226/194; 29/110; 384/277, 444; 68/13 R; 8/151, 158; 118/712, 713

[56] References Cited

U.S. PATENT DOCUMENTS

| | | | |
|---|---|---|---|
| 1,645,041 | 10/1927 | Clarkson, Jr. | 384/444 |
| 1,789,452 | 1/1931 | Schweitzer | 162/DIG. 6 |
| 1,989,627 | 1/1935 | Sage | 324/65 R |
| 2,713,662 | 7/1955 | Hart | 324/65 R |
| 2,849,676 | 8/1958 | Collins | 324/65 R |
| 2,870,405 | 1/1959 | Wright et al. | 324/65 R |
| 2,927,363 | 3/1960 | Park . | |
| 3,297,945 | 1/1967 | Strandberg, Jr. | 324/65 R |
| 3,384,815 | 5/1968 | Lyall et al. | 324/65 R |
| 3,541,437 | 11/1970 | Ahrweiler | 324/65 R |
| 3,732,435 | 5/1973 | Strandberg, Jr. et al. | 307/118 |
| 3,823,371 | 7/1974 | Lippke | 162/263 |
| 4,156,843 | 5/1979 | Strandberg, Jr. et al. | 324/58.5 B |

Primary Examiner—Philip R. Coe
Attorney, Agent, or Firm—Nixon & Vanderhye

[57] ABSTRACT

An improved fabric moisture monitoring system and method particularly adapted for use on a slasher unit comprises utilizing the delivery roller associated with the conventional slasher unit to facilitate moisture monitoring. Both ends of the delivery roller are electrically isolated and either end is connected to a moisture monitoring apparatus.

3 Claims, 3 Drawing Figures

SLASHER MOISTURE MONITORING SYSTEM

BACKGROUND OF THE INVENTION

The present invention generally relates to an improved system for monitoring the liquid content retained in a fabric material during the processing of such material. More particularly, the present invention relates to an improved monitoring system for detecting the retained liquid in a fabric warp wherein the detection of the retained liquid is accomplished substantially across the entire width of the warp yarns.

The processing of textile materials often requires that they be treated with a liquid. For example, in dyeing operations, the textile material is treated in a liquid dye bath so that the dye coloring can be effectively transferred to the textile material.

Additionally, the textile material may be sized prior to weaving filler yarns into the warp. Sizing of textile material is generally accomplished by way of a sizing machine (commonly referred to as a "slasher unit") which coats the yarn with a sizing material, such as, starch, gelatin, oil, wax, or manmade polymers such as polyvinyl alcohol, polystyrene, polyacrylic acid, polyacetates, or the like. The sizing is utilized during the weaving process to protect the warp yarns from the abrasive tendencies of the weaving process. Accordingly, after the weaving is accomplished, the sizing is washed or otherwise removed from the warp yarn, having thus served its intended purpose.

Since the amount of retained liquid in the yarn is correlated to the desired properties to be imparted to the yarn during processing, it is extremely important for the devices which treat the yarn with liquid to operate in a proper manner so that the time during which the yarn is in contact with the liquid is sufficient for the desired results. For example, in a slasher unit, it is desirable to size the yarn so that the abrasive consequences of weaving do not affect the quality of the finished product. Thus, too little sizing applied to the yarn during the sizing process will, necessarily, defeat the purpose of the sizing and may have the deleterious effect of having portions of the warp yarn break or fray due to the friction encountered during weaving. Such an effect would result in an unacceptable product and, of course, must be avoided.

The measurement of retained liquid in the yarn after it has been subjected to the sizing process is correlated to the sufficiency of the sizing operation. Accordingly, by controlling the retained liquid or the moisture content of the yarn, the proper amount of sizing will be imparted to the yarn.

It has been proposed in the art to utilize various contrivances for measuring moisture in order to control the processing parameters of a liquid process. However, prior art devices which are utilized to measure the moisture and thereby control the processing of the yarn in a liquid environment are primarily intended to be utilized as adjuncts or auxiliary appendages to the standard equipment utilized in the textile industry.

For example, in U.S. Pat. No. 3,732,435 to Strandberg, Jr. et al. (the entire disclosure of which is incorporated herein by reference herein) moisture detectors are utilized in conjunction with a moisture monitoring apparatus wherein the detectors are in the form of small rollers which measure only a few limited spans along the warp width. In practice, the moisture detectors of U.S. Pat. No. 3,732,435 are in the form of small rollers and are positioned over the warp yarn by means of a supporting beam having the rollers attached to the beam. These rollers are then allowed to bear upon the top of the warp and, as such, impart a downward pressure to the warp yarns. Of course, with fine denier yarns comprising the warp, such a pressure may have the deleterious effect of causing yarn breakage or excess wear. Additionally, such rollers may provide an unnecessary abrasive action to the sized warp yarns with the possible result that the yarns may not be able to withstand further abrasive action downstream.

While the measurement of retained liquid in yarns after being treated with sizing is mentioned above, it should be appreciated by those in the art that other processing techniques utilizing liquid also have a correlation between the desired property to be imparted to the yarn and the retained moisture of the yarn after the processing sequence. Additionally, the retained moisture of the yarn can be measured subsequent to drying operations so that the yarn can be properly dried and, therefore, prepared for subsequent processing operations.

Accordingly, it has been desirous to obtain a measurement of the moisture retained across the entire warp width without the deleterious effects mentioned above and to this end the present invention is directed.

SUMMARY OF THE PRESENT INVENTION

According to the present invention, there is provided a means by which a detection of the retained liquid in the warp can be monitored across the entire width thereof. The monitoring system according to the present invention does not utilize any auxiliary supporting equipment, such as provided in prior art arrangements thereby reducing the cost of installing and maintaining such moisture monitoring equipment.

According to the present invention, both ends of a delivery roller conventionally supplied as an integral component of most slasher units are electrically isolated and either one of the two ends would then be connected to a moisture measuring device. Very little modification needs to be made to the conventional delivery roller, thereby enabling efficient conversion of existing slasher units. Additionally, the full width nature of conventional delivery rollers of slasher units provides continuous monitoring of the moisture content thereof across the entire width of the yarn when modified according to the present invention. Since the slasher unit delivery rollers are conventionally utilized to direct the warp yarns to a subsequent processing step, such as, to beam the warp yarns in preparation for weaving, the conversion of such delivery rollers to a moisture detector does not place any additional strain or abrasion on the warp yarns.

Thus, according to the present invention, the conventional delivery rollers serve a dual function. That is, the delivery rollers are utilized according to their conventional intended function (e.g. directing and guiding the moving warp) and as a means for detecting moisture in the moving warp. The later function is novel to the present invention. The combined dual utility of the conventional delivery roller yields the significant advantage of totally eliminating auxiliary moisture detecting structures yet, at the same time, provides improved moisture detecting capability compared to prior art devices. Additionally, significant savings can be realized when consideration is given to the superfluous costs associated with the mounting and installation equipment utilized with such conventional moisture detectors.

Accordingly, the problems associated with conventional moisture monitoring equipment and, particularly, the moisture detector rolls thereof, are completely alleviated according to the present invention.

While reference has been or will be made herein to the delivery rollers of a slasher unit, it should be appreciated that the present invention may be modified by those in the art without departing from the scope of the appended claims. Accordingly, it is conceivable that the present invention can be utilized with satisfactory results in dyeing operations, washing operations, drying operations, or other processing techniques where the liquid content of the fabric is to be detected, measured and/or controlled. Thus, the reference herein to delivery rollers on a slasher unit should be considered as being an exemplary embodiment only, and nonlimiting.

DETAILED DESCRIPTION OF THE PREFERRED EXEMPLARY EMBODIMENT

Figures 2, 3:
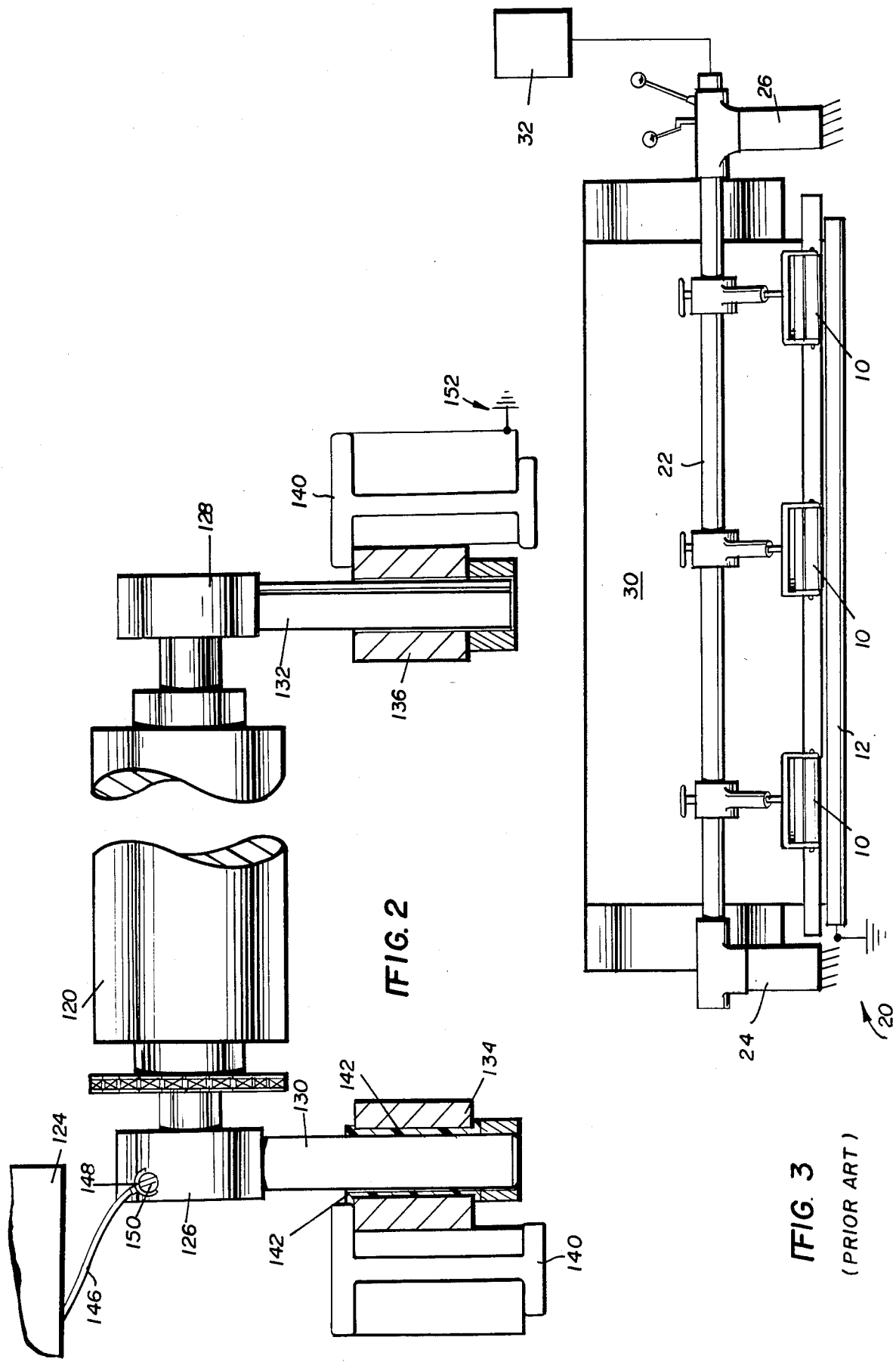
FIG. 2 depicts a front elevational view of a slasher unit delivery roller depicting the present invention in greater detail.
FIG. 3 depicts a prior art mechanism for detecting and monitoring the moisture content in warp yarns.

FIG. 3 depicts a prior art arrangement for detecting retained liquid and/or moisture in the warp yarns. The detector rollers 10 are generally those type of rollers which are, in practice, conventionally utilized with the moisture monitor Model M-601 manufactured by Strandberg Engineering Laboratories, Inc., Greensboro, N.C., under U.S. Pat. No. 3,732,435.

As can be seen by referring to FIG. 3, detector rollers 10 are transversely mounted above one of the delivery rollers 12 at the end of a conventional slasher unit 20. Mounting bar 22 is mounted between opposite frame members 24, 26, respectively, located on either side of the moving warp 30 and extends above delivery roller 12.

Detector rollers 10 are mounted to the detector roll mounting bar 22 so that each can freely rotate about the central axis of bar 22. Accordingly, the weight of detector rollers 10 according to this prior art device is brought into full force against the top portion of the yarns in the warp 30. The detector rollers 10 are of relatively small length, so that only limited segments of the warp 30 are monitored for their retained moisture.

The detector rollers 10 of the prior art are electrically coupled to a moisture detector unit 32 having circuitry designed to detect and monitor the retained moisture in the warp. (See, U.S. Pat. No. 3,732,435)

Figure 1:
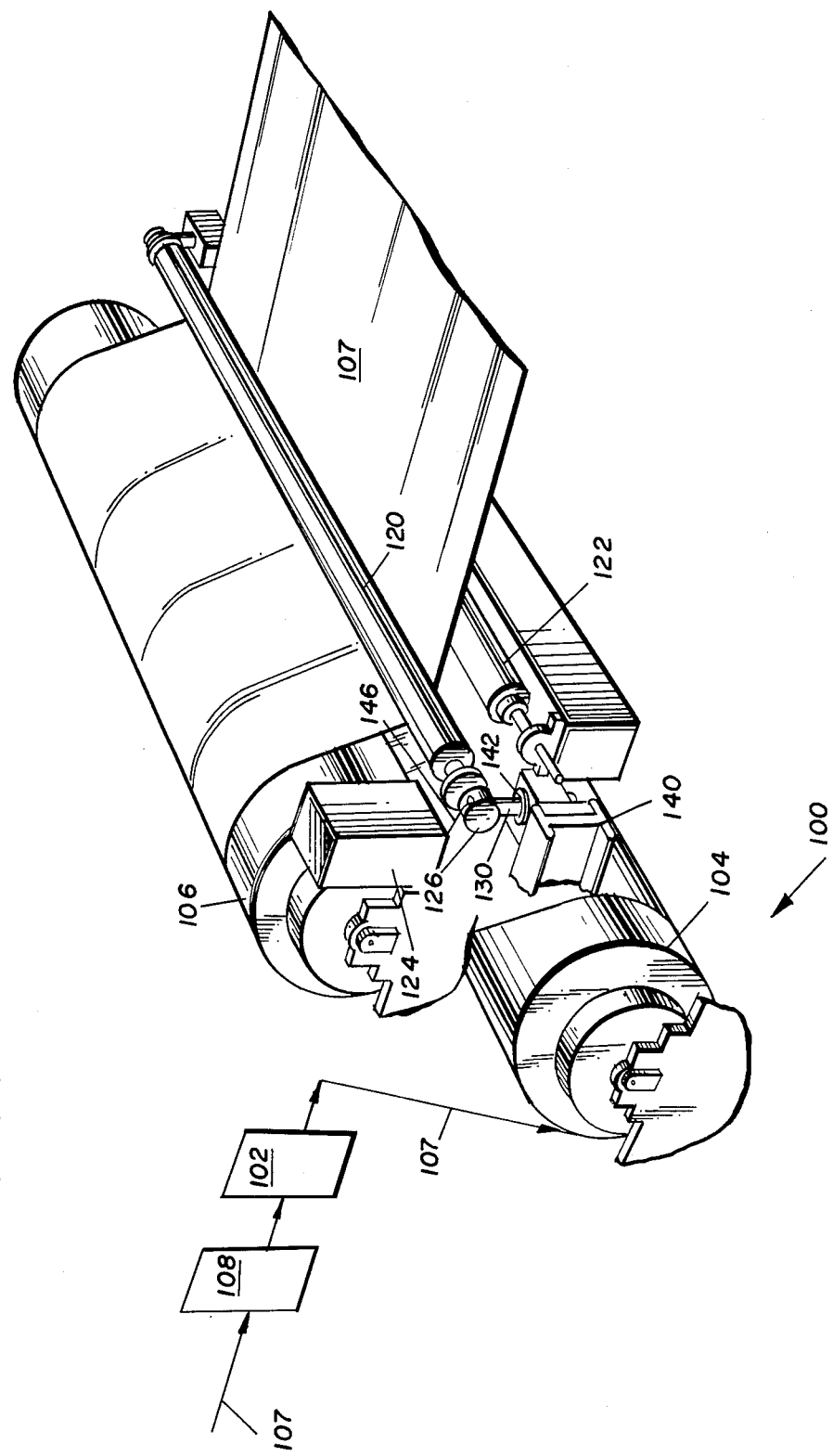
FIG. 1 depicts a partial diagrammatic perspective view of the end portion of a conventional slasher unit showing the delivery rollers thereof modified according to the teaching of the present invention.

According to the present invention a continuous, full width monitoring of the retained moisture in the warp can be obtained. Referring to FIG. 1, the typical slasher unit 100 comprises a predrier unit (schematically shown as 102 in FIG. 1) upstream of a plurality of drying cylinders commonly referred to as the "dry can section" (two representative drying cylinders are shown in FIG. 1 at 104 and 106, respectively). The predrier unit 102 is located downstream of the unit which applies the sizing to the yarns in the warp 107 (shown schematically at 108 in FIG. 1). Downstream of the last drying cylinder 106 and in close proximity thereto, there are provided delivery rollers 120, 122 which are in and of themselves, conventional to most textile machines. Closely adjacent to the delivery rollers 120, 122 is a moisture monitor 124, such as, the Strandberg moisture monitor Model M-601, as hereinbefore referred.

FIG. 2 depicts a more detailed view of the modification according to the present invention. In particular, delivery roller 120 is provided so that it is journalled between two bearing housings 126, 128 across the entire width of the warp. Each delivery roll bearing housing 126, 128 is supported above warp 107 by way of a support rod 130, 132, respectively, housed in support sleeves 134, 136, respectively, which in turn, are fixedly secured to the dry can section frame (noted generally as 140 in FIG. 2).

Disposed around the periphery of support arm 130, there is provided according to the present invention electrical insulation material 142 so that both ends of delivery roller 120 are electrically isolated thereby preventing short-circuit grounding. A suitable insulating material can be, for example, nylon, bakelite, rubber or any other material which exhibits electrical insulating properties. However, for the present embodiment, it is preferred to use substantially rigid bushings of nylon interposed between support arm 130 and sleeve 134 as shown in FIG. 2.

With both ends of delivery roller 120 electrically isolated as described above, the electronic moisture monitor 124 can be connected to delivery roller 120 so that the entire width thereof can be utilized as a detector for retained liquid in the warp yarns. In the embodiment depicted in FIG. 2, this connection is made between moisture monitor 124 and bearing housing 126 by way of suitable connector means, such as, copper lead 146 having a connecting portion 148 and attached to bearing housing 126 by means of a screw 150. At no time should the delivery roll be grounded.

Thus, the internal metallic parts of delivery roller 120 will necessarily conduct sufficient electrical current generated by the moisture monitor 124 and detect the retained moisture in the warp due to the resistance thereof to electrical current. This resistance is detected by the moisture monitor and is responsively transformed into a readable scale or the like. (See, U.S. Pat. No. 3,732,435 at columns 6–11)

Accordingly, since the modification according to the present invention utilizes a determination and measurement of the resistance as a function of the retained liquid in the warp yarns, it should be appreciated that the delivery roller should be constructed of an electrically conductive material, such as metal.

Additionally, while reference has been made to the delivery roller of a slasher unit positioned after the dry can section thereof, it should be appreciated that the present invention can be satisfactorily utilized by modifying existing rollers wherever it is desired to control or detect the moisture content in a fabric process.

As will be appreciated, the moisture monitor can be utilized to serve several functions. First, a direct reading of the moisture content in the yarns of the warp can be used by an operator of the slasher unit to manually adjust the speed of the fabric as it moves through the sizing and drying operations. However, in today's automated textile mill, it is more preferable to connect the moisture monitor with suitable means for controlling the speed at which the warp moves through the sizing operation.

For example, a variable drive means coupled to the drive rollers in which the speed of the yarn can be increased or decreased depending upon the detected moisture content can be effected. Of course, if the moisture monitor detects that the retained moisture in the yarns of the warp is too high, the resulting signal will cause the drive means to increase in speed thereby increasing the speed of the warp as it moves through the liquid. Thus, the retention time of the warp with the liquid will be decreased thereby decreasing the liquid which is retained by the yarn warps. Conversely, if the moisture monitor detects that the retained moisture in the yarns of the warp is too low, the responsive signal will cause the drive means to reduce speed to such an extent that the proper moisture may be increased in the yarns of the warp. In such a manner, the system as hereinabove described can be utilized to control the moisture content of the warp yarns within a predetermined range of set values.

While the above invention has been herein described in what is presently conceived to be the most practical embodiment thereof, modifications thereof may be made within the scope of the present invention, which scope should be accorded the broadest interpretation of the appended claims so as to encompass all equivalent assemblies, systems and/or devices.

What is claimed is:

1. A system for monitoring the moisture content of a web substantially across the entire width thereof, comprising:

roll means disposed substantially across the width of a web for detecting the moisture content thereof as the web continuously moves in contact with a predetermined portion of said roll means;

means for moving said web continuously in contact with a predetermined portion of said roll means;

means for electrically isolating both ends of said roll means, said electrically isolating means comprising: first and second bearing means, one operatively mounted to each end of said roll means, for providing for rotation of said roll means about an axis, and with respect to a housing of each of said bearing means; first and second support rods, one extending radially outwardly from each of said first and second bearing means; first and second support sleeves for mounting each of said first and second support rods; and a sleeve of electrical isolation material operatively disposed between each of said first and second support rods and its respective support sleeves; and means for detecting the amount of liquid retained by the web at said roll means, said detecting means being electrically coupled to said roll means at one end thereof.

2. A system as recited in claim 1 wherein each of said sleeves of insulated material comprises a substantially rigid nylon bushing.

3. A system as recited in claim 1 wherein said bearing means are electrically conductive, including housings therefor, and wherein said detecting means is electrically coupled to one of said bearing means housings by a screw and a lead wire.

* * * * *